United States Patent

Wicks et al.

[11] Patent Number: 5,872,505
[45] Date of Patent: Feb. 16, 1999

[54] MEDICATION ALERT PAGER AND PAGING SYSTEM

[75] Inventors: James E. Wicks, San Francisco, Calif.; Eduardo Sciammarella, Hoboken, N.J.

[73] Assignees: Sony Corporation, Tokyo, Japan; Sony Electronics, Inc., Park Ridge, N.J.

[21] Appl. No.: 810,811

[22] Filed: Mar. 6, 1997

[51] Int. Cl.$^6$ .............................. H04Q 1/30; A61B 5/04
[52] U.S. Cl. .................................. 340/311.1; 340/309.15; 340/309.4; 128/732; 128/904
[58] Field of Search ........................... 340/309.15, 309.4, 340/309.5, 311.1, 573, 825.36, 825.44, 407.1; 128/732, 904, 905; 359/811

[56] References Cited

U.S. PATENT DOCUMENTS

| | | | |
|---|---|---|---|
| 4,223,801 | 9/1980 | Carlson | 221/3 |
| 4,415,065 | 11/1983 | Sandstedt | 395/234 |
| 4,626,105 | 12/1986 | Miller | 340/309.4 |
| 4,951,039 | 8/1990 | Schwendeman et al. | 340/825.44 |
| 5,005,013 | 4/1991 | Tsukamoto et al. | 340/825.44 |
| 5,088,056 | 2/1992 | McIntosh et al. | 340/309.15 |
| 5,173,688 | 12/1992 | DeLuca et al. | 340/825.44 |
| 5,319,355 | 6/1994 | Russek | 340/311.1 |
| 5,331,431 | 7/1994 | Jasinski | 358/462 |
| 5,446,678 | 8/1995 | Saltztein et al. | 364/514 R |
| 5,452,356 | 9/1995 | Albert | 340/825.44 |
| 5,481,255 | 1/1996 | Albert et al. | 340/825.55 |
| 5,485,318 | 1/1996 | Lebby et al. | 359/811 |
| 5,491,785 | 2/1996 | Robson et al. | 395/162 |
| 5,495,344 | 2/1996 | Callaway, Jr. et al. | 358/407 |
| 5,508,695 | 4/1996 | Nelson et al. | 340/825.37 |
| 5,535,428 | 7/1996 | King et al. | 455/38.4 |
| 5,594,786 | 1/1997 | Chaco et al. | 128/904 |
| 5,596,994 | 1/1997 | Bro | 128/732 |

*Primary Examiner*—Jeffery A. Hofsass
*Assistant Examiner*—Van T. Trieu
*Attorney, Agent, or Firm*—Ronald P. Kananen

[57] ABSTRACT

A novel pager and paging system assist a patient with treatment reminders. A database containing information about the treatment regimen or appointment schedule of a patient is maintained by a paging system service provider. At appropriate times, the paging system transmits reminders to the patient's pager that a treatment is to be taken or an appointment kept. The reminder may further include instructions or information to assist the patient in taking the treatment or keeping the appointment.

6 Claims, 3 Drawing Sheets

MEDICATION ALERT PAGER AND PAGING SYSTEM

FIELD OF THE INVENTION

The present invention relates generally to the field of wireless pagers. More particularly, the present invention relates to the application of wireless pager technology to provide timely reminders to patients who need to maintain a medication regimen.

BACKGROUND OF THE INVENTION

Portable radio receivers and transceivers, such as wireless pagers, have become increasingly popular as a means of communication. Pagers are typically carried by users who wish or need to receive communications when they are away from a telephone or computer, or are unable to predict where they may be reached at a given time.

In general, the user of a pager purchases the unit and enters into a contract with a service provider. As shown in FIG. 1, when someone 12 wishes to page a particular user, they contact the user's service provider 11, identify the user to be paged (perhaps with a personal identification number), and may give a message to the service provider 11 that is to be broadcast to the user's pager 15.

The service provider 11 maintains a network of radio transceiver base stations 13, 14 which are spread throughout the service area covered by the service provider. The transmitting base stations 13 are distributed so that transmissions from at least one base station can be received by a pager 15 anywhere in the service area.

In a simplistic system, when the service provider 11 receives a request to page a user 15, the page is broadcast by all the base stations 13 in the system. Thus, if the pager 15 is located anywhere in the service area, it will receive the page. The pager 15 will then alert the user that a page has been received with, for example, an audible or vibratory alert signal.

In a more sophisticated system, the pager 15 may have the capability to not only receive a transmission from the service provider's system, but may have the capability to transmit an answer back to the system. This is referred to as two-way paging.

With these advances, the usefulness of pagers as a means of communication has expanded rapidly. Service providers have encouraged this expansion by experimenting with pagers as a means to disseminate information of interest to pager users. For example, as described in U.S. Pat. No. 5,508,695 to Nelson et al., incorporated herein by reference, a one-way pager system is used to relay sports or financial information to a pager user who has contracted with the service provider for that service.

However, there are many potential, undiscovered applications of pager technology which may provide pager users with, as yet unheard of, abilities to communicate. This is particularly true of the developing two-way pager systems. Accordingly, there is a need for improved methods and applications of pager technology to meet the information and communication demands of pager users.

Similar to the growth in the field of communications, modern medicine constantly provides new treatments, techniques and drugs to improve health and quality of life. However, advanced medical care may often require a complex and regular regimen of a variety of medications and/or frequent appointments with a medical practitioner. For some patients, particularly the elderly, who requires such therapy, the array of medications and/or office visits may be confusing or difficult to maintain. Accordingly, there is a need to simply the burden complex medical therapies impose on patients.

SUMMARY OF THE INVENTION

It is an object of the present invention to meet the above-identified needs and others. Particularly, it is an object of the present invention to provide a pager technology in which a pager user can use a pager to receive timely reminders and instructions for taking prescribed medications. If is a further object of the present invention to provide a pager technology with which a pager user can receive timely reminders regarding appointments with doctors, therapists, etc.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve the stated and other objects of the present invention, as embodied and described below, the invention may encompass a paging system having: a central processor; a treatment information database containing treatment information for at least one person; and at least one transmitter for transmitting data to a pager. The processor accesses the treatment database and transmits data to a pager based on the information in the database. The transmission comprises information regarding a medical treatment to be received by the person. The transmission is timed so as to serve as a reminder of the treatment.

The treatment may be a treatment which is self-administered by the person, or administered at an appointed time by a medical practitioner.

According to the principles of the present invention, the information transmitted may be abbreviated. The abbreviated information may specify a color and quantity of a pill to be taken.

The present invention may also encompass a pager having: a display; an antenna for receiving transmissions from a paging system; a controller for displaying the transmissions on the display; and a magnifying lens disposed over the display. The invention may further include a necklace attached to the pager to allow the pager to be worn around a person's neck.

Additionally, the pager of the present invention may including an emergency alert button. When the button is pressed, the controller transmits a distress signal to the paging system.

The present invention may also encompass a method of using a paging system to remind a patient about a treatment to be received by compiling a treatment information database containing treatment information for at least one person; accessing the treatment information database with a processor; transmitting a transmission to a pager with the paging system, the transmission comprising information from the database regarding a treatment to be received by the person; and timing the transmission so as to serve as a reminder of the treatment. Again, the treatment may be self-administered or administered at an appointed time by a medical practitioner.

The method may also including abbreviating the information in the transmission. The abbreviated information may specify a color and quantity of a pill to be taken.

Finally, the present invention may further encompass a method of using a pager to regulate medical treatments by receiving a transmission regarding a medical treatment from a paging system with an antenna of the pager; displaying the transmission on a display of the pager; magnifying the display with a magnifying lens disposed over the display. The present method may further include wearing the pager around a neck by a necklace attached to the pager.

The present method may continue by providing the pager with an emergency alert button; and transmitting an emergency distress signal to the paging system when the button is pressed.

BRIEF DESCRIPTION OF THE DRAWINGS

The accompanying drawings illustrate the present invention and are a part of the specification. Together with the following description, the drawings demonstrate and explain the principles of the present invention. In the drawings.

DETAILED DESCRIPTION OF THE PREFERRED EMBODIMENT

Using the drawings, the preferred embodiment of the present invention will now be described.

As explained above, a paging system can provide either one- or two-way paging. While the principles of the present invention could certainly be used with a two-way paging system, in the preferred embodiment, a less expensive one-way system is employed.

Figure 3:
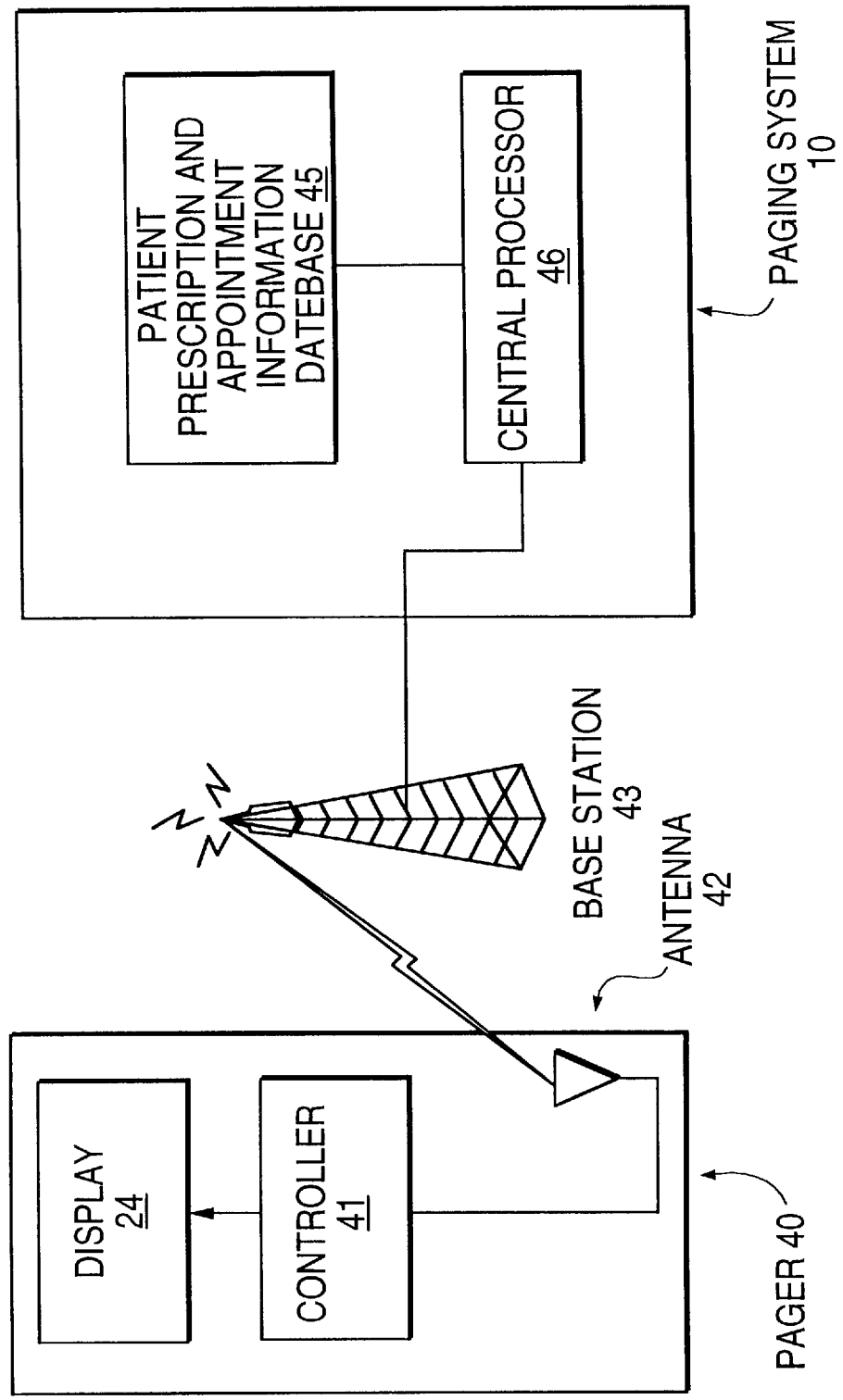
FIG. 3 is a diagram of the components of the pager and paging system according to the present invention.

FIG. 3 illustrates a one-way pager 40 and paging system 10 according to the principles of the present invention. The pager 40 includes a display 24, a controller 41 and an antenna 42. The controller 41 receives transmissions from the paging system 10 via antenna 42 and drives display 24. The paging system 10 is provided with a central processor 46 and a database 45 of prescription and appointment information for patients who have subscribed to the paging system's treatment reminder service.

The information in database 45 will contain such information as when a patient should take pills, what kind of pills to take, and how many pills should be taken. The database may also include similar information regarding any other type of treatment. Examples include, but are not limited to, injections, inhalants, elixirs, bandages, wound irrigation, heat or cold therapy, drops, etc. Finally, the database may also include information about appointments the patient has with doctors, therapists or other medical practitioners.

The information in database 45 may be compiled by the service provider in a number of ways. For example, when a patient wishes to subscribe to the paging system's treatment reminder service, that patient may provide detailed information about the drug and treatment regimens or appointments which the patient must keep. Additionally, the paging system service provider may be in contact with the patient's doctor, Health Maintenance organization, pharmacy, therapist, etc. and compile from those direct sources the necessary information regarding the patient's treatment.

The central processor 46 of the paging system 10 monitors the patient information database 45. At appropriate times, the processor 46 will transmit a treatment reminder. In the case of a self-treatment, the reminder should contain sufficient information to allow the patient to easily affect the treatment. For example, in the case of taking pills, the message may specify the number and type of pills to be taken.

Figure 1:
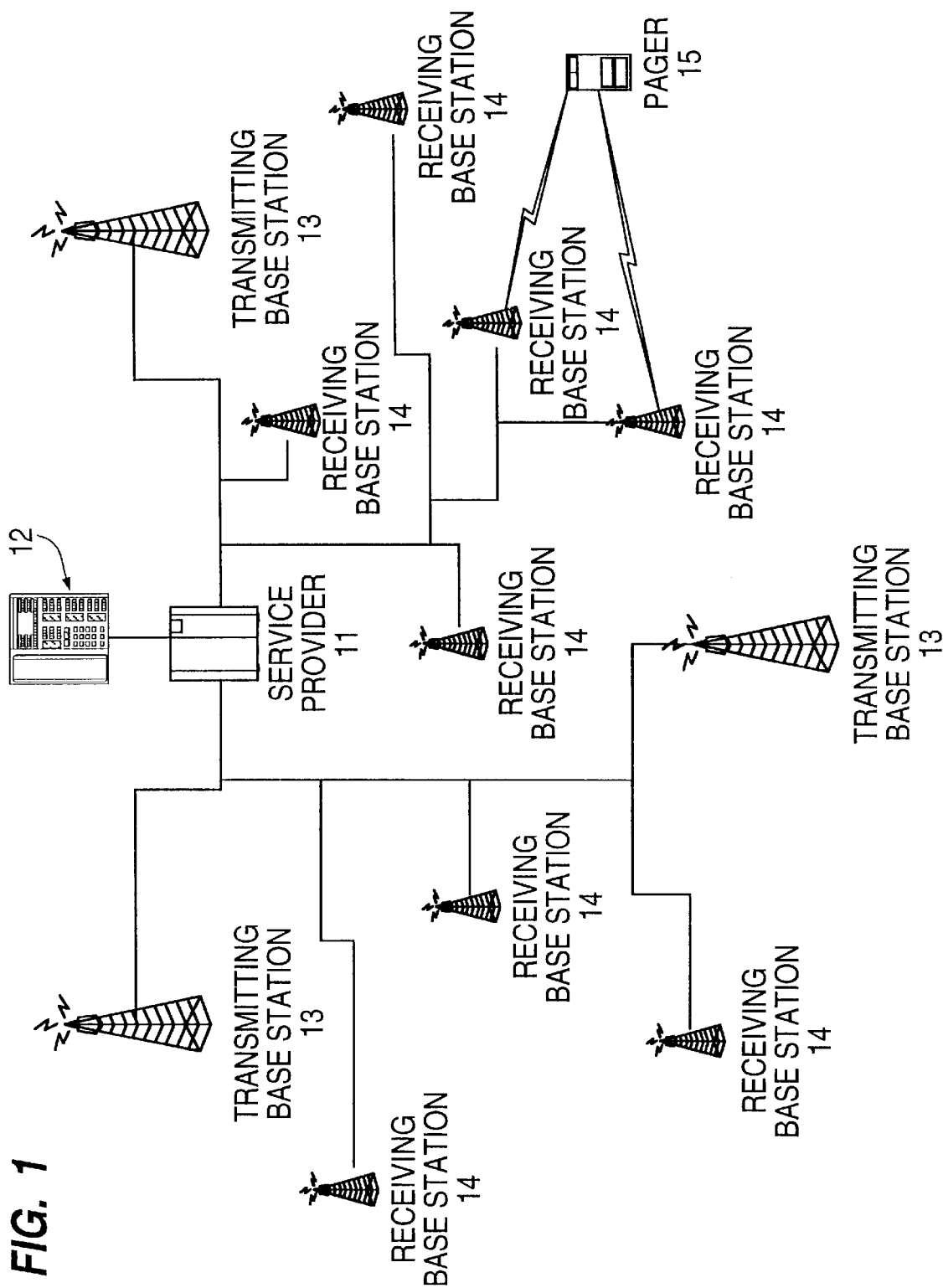
FIG. 1 is a schematic diagram of a conventional paging network with which the present invention may be practiced.
Figure 2:
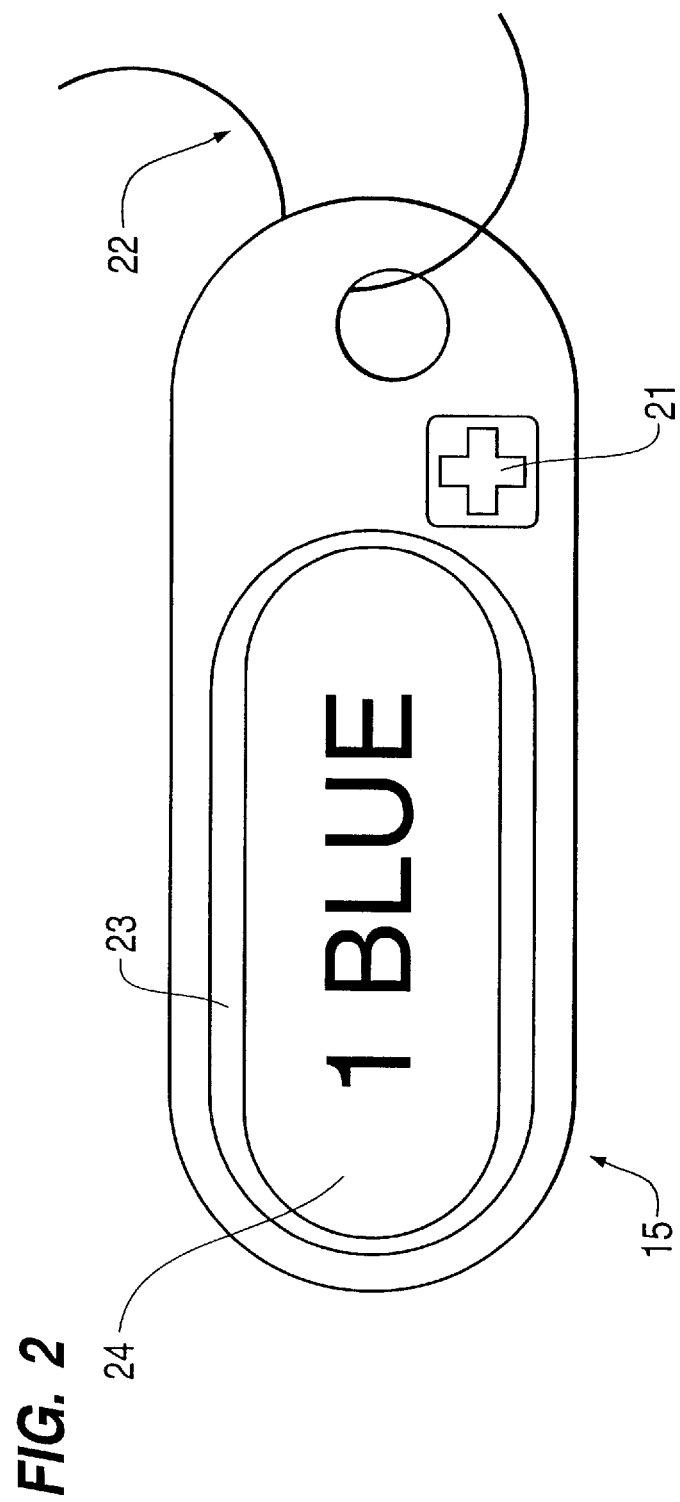
FIG. 2 is a diagram of a pager according to the principles of the present invention.

As illustrated in FIG. 2, the reminder may further be simplified to a message such as "1 BLUE," meaning take one blue pill. Such simplified directions may be particularly useful for the elderly who may need to take a confusing and complex variety of different pills at different times.

In the case of appointments with medical practitioners, the reminder may include such information as the name, address and phone number of the practitioner and the time of the appointment.

The reminder, transmitted via base station 43, is received by pager 40. The pager 40 then alerts the patient that a message has been received with either a vibratory or audible alert signal. The reminder is then displayed on display 24. In the case of a treatment appointment with a medical practitioner, the central processor 46 will transmit the reminder sufficiently in advance of the appointment so that the patient has time to arrange to keep the appointment.

FIG. 2 illustrates a pager particularly adapted according to the principles of the present invention. The pager 15 includes a display 24 for displaying treatment reminders transmitted by the paging system.

Pager 15 may also include a necklace 22 so that the pager can be work around the neck and conveniently accessible at all times. The necklace 22 may be a cord, preferably nylon. Alternatively, the pager could be provided with a belt clip, etc.

According to the principles of the present invention, if the patient using pager 15 is elderly or for other reasons has poor eyesight, a magnifying lens 23 may be provided over display 24 to magnify the treatment reminder so that it is easily read by the patient. The displayed message is preferably magnified by a factor of 3.

Finally, if the present invention is practiced with a two-way paging system, the pager may be provided with an emergency alert button 21. When pressed, the emergency alert button 21 causes the pager 15 to transmit a distress signal to the paging system 10. The distress signal is the relayed to a hospital or ambulance as appropriate. Accordingly, the patient who may be in distress and unable to otherwise summon assistance can call for help using the pager of the present invention.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A paging system comprising:

a central processor;

a treatment information database containing treatment information for at least one person; and at least one transmitter for transmitting data to a pager;

wherein said processor accesses said database and transmits a transmission to a pager based on the information in said database, wherein said transmission is received by a medical practitioner, comprises information regarding a medical treatment to be received by said person, and is timed so as to serve as a reminder of said treatment;

wherein said treatment is to be administered at an appointed time by said medical practitioner.

2. A paging system as claimed in claim 1, wherein said transmitted information is abbreviated.

3. The paging system as claimed in claim 1, further comprising a pager comprising an antenna for receiving said transmission and a display for displaying said information.

4. A method of using a paging system to remind a patient about a treatment to be received comprising:

compiling a treatment information database containing treatment information for at least one person;

accessing said treatment information database with a processor;

transmitting a transmission to a pager with said paging system, said transmission comprising information from said database regarding a treatment to be received by said person;

timing said transmission so as to serve as a reminder to a medical practitioner of said treatment, wherein said treatment is to be administered at an appointed time by said medical practitioner.

5. A method as claimed in claim 4, further comprising abbreviating said information in said transmission.

6. The method as claimed in claim 4, further comprising:

receiving said transmission with an antenna of a pager;

displaying said information with a display of said pager.

* * * * *